United States Patent [19]

Dabney et al.

[11] 3,945,380
[45] Mar. 23, 1976

[54] PLASMAPHERESIS ASSEMBLY

[75] Inventors: William C. Dabney, Oakland; Basil L. Kristoff, Moraga; Robert D. Tuseth, Alameda; John H. Hink, Orinda, all of Calif.

[73] Assignee: Cutter Laboratories, Inc., Berkeley, Calif.

[22] Filed: Aug. 21, 1974

[21] Appl. No.: 499,297

[52] U.S. Cl. ......... 128/214 R; 128/214 D; 137/610; 251/342
[51] Int. Cl.² ......................................... A61M 5/00
[58] Field of Search ........ 128/214 R, 214 A, 214 B, 128/214 C, 214 D, 214.2, 274, 213; 251/342; 137/608, 610

[56] References Cited
UNITED STATES PATENTS

| | | | |
|---|---|---|---|
| 2,674,265 | 4/1954 | Dennis | 137/610 |
| 2,862,497 | 12/1958 | Pagano | 128/274 X |
| 3,459,182 | 8/1969 | Naftulin | 128/214 R |
| 3,625,212 | 12/1971 | Rosenberg et al. | 128/214 R |
| 3,707,972 | 1/1973 | Villari et al. | 128/274 X |
| 3,782,382 | 1/1974 | Naftulin | 128/214 R |
| 3,800,799 | 4/1974 | McWhorter | 128/274 X |
| 3,802,662 | 4/1974 | Viguier | 251/342 |

*Primary Examiner*—Dalton L. Truluck
*Attorney, Agent, or Firm*—Gardiner, Sixbey, Bradford & Carlson

[57] ABSTRACT

The plasmapheresis assembly includes a novel Y connector valving structure to replace conventional tube clamps. This valving structure eliminates dead spaces for blood to collect and clot and provides a fluid tight seal during heat sterilization without causing deformation of the tubing for the assembly. Possible erroneous connection of assembly components with resultant contamination is eliminated by the use of unique mating connectors in place of spikes or needle connectors. These mating connectors are employed in a simple and efficient blood bag construction to provide substantially rigid access ports to facilitate rapid manual manipulation of the blood bags.

22 Claims, 3 Drawing Figures

PLASMAPHERESIS ASSEMBLY

BACKGROUND OF THE INVENTION

Modern plasmapheresis techniques for collecting blood plasma from a donor permit a donor to give two units of blood (aout 600 ml. each) at one time, but after the withdrawal of one unit of blood, the red cells must be returned to the donor before the second unit is withdrawn. In early blood collection equipment, it was necessary to disconnect a first blood container from a blood flow tube after the return of the red blood cells so that the second blood container could subsequently be connected to the blood flow tube to return the red cells obtained from the second unit of blood.

To rectify this situation, a blood administration method and system was designed wherein the containers for the first and second batches of red blood cells were connected to a different inlet for the same blood flow tube. This administration set and the blood collection assembly employed therewith is illustrated by U.S. Pat. No. 3,459,182 to Henry Naftulin. The blood administration system shown in the Naftulin patent obviates the necessity to disconnect a first blood container from a blood flow tube before red cells are returned to the donor from a second blood container, and thus provides a sterile and more effective administration set. However, the blood collection system disclosed by the Naftulin patent is typical of presently known blood collection systems currently employed for the withdrawal of whole blood from a donor. In such systems, two flexible collection bags, each containing about 50 or 60 ml. of sodium citrate solution are each connected by tubing to a separate Y connector. One of these Y connectors communicates through a tube with a needle for drawing blood from the donor, while the second Y connector is joined both to the first Y connector and also to an administration set for saline solution and the red blood cells.

To use such prior blood collection sets, the phlebotomy or venipuncture needle is placed in the vein of a donor after first clamping off the connecting tube between one blood bag and the associated Y connector with a hemostat. Additional clamps or hemostats are also placed on the connection between the blood administration set and the Y connector joined therewith. Control of the blood collection process is accomplished by manually moving the hemostats to selectively clamp off other tubes in the collection set at desired times. This process is not only time consuming, but is subject to error if a hemostat is not secured to properly shut off a tube.

Even more important is the necessity to properly position the hemostat between a blood collection bag which is not in use and the venipuncture needle. It is a natural practice to place the hemostat at some position along the tube between the blood collection bag and the associated Y connector, for this placement is relatively easy to accomplish in a short time. However, if the hemostat is not actually placed on the Y connector to close off one branch thereof to an unused blood collection bag, blood can collect in the dead space between the Y connector and the hemostat. This static blood is likely to clot during portions of the procedure when there is little or no flow through the adjacent branches of the Y connector. Then, when the hemostat is released, the clot will prevent flow in the newly opened branch to the blood bag or, in the alternative, may break loose to clog the venipuncture needle. The same problem results when valving means are provided at the inlet to the blood collection bag.

The blood collection bags or containers employed with a blood collection set are normally disposed after use, and such containers, as disclosed by the aforemention Naftulin patent, often constitute a bag of thin, flexible material having an inlet tube sealed thereto for blood and two additional access ports. These access ports are usually identical and consist of a short tube having a pierceable diaphragm at the inner end thereof; sterility being maintained by capping the outer end with a frangible cap as illustrated in U.S. Pat. No. 3,509,879 to L. N. Bathish et al. The diaphragm must be pierced and entered by a needle or spike in order to add or remove any solution or fluid content from the container. Flexible containers of this type are well known to the prior art as illustrated by U.S. Pat. Nos. 2,894,510 and 2,950,716 to D. Bellamy, Jr., as well as a second U.S. Pat. No. 3,782,382 to Henry Naftulin et al.

The structure of prior art blood collection bags or containers results in some inherent problems when the bags must be handled in the manner required by conventional plasmapheresis techniques. For example, the bags are extremely flexible, and when filled with fluid are difficult to handle and hold. The short access ports projecting from the body of the bag are formed of flexible tubing and are difficult to grasp. These ports are even more difficult to use for purposes of stabilizing the bag while a needle is inserted through the pierceable diaphragm closing a port. Often, the bag shifts during this piercing operation and the needle or spike penetrates the sidewalls of the bag or the access port tube. This causes the contents of the bag to leak and sometimes results in injury to the fingers or hand of the operator. Also, an operator attempting to rapidly manipulate two blood collection bags and properly pierce and connect four separate access ports is very likely to pierce the wrong port and accomplish an erroneous connection. Once this is done, the sterility of the fluid in an associated collection container can be destroyed.

It is a primary object of the present invention to provide a novel and improved plasmapheresis assembly which requires no pierceable needle connections to accomplish the addition or removal of fluids from portions of the system.

Another object of the present invention is to provide a novel and improved plasmapheresis assembly which incorporates unique container access connectors and mating conduit connectors to insure that proper connections are made to accomplish a plasmapheresis operation.

A further object of the present invention is to provide a novel and improved plasmapheresis assembly employing externally operated Y valve units to positively close the branch conduits of the assembly and preclude the formation of dead spaces where blood clots may form.

Another object of the present invention is to provide a novel and improved plasmapheresis assembly which includes flexible fluid collection bags having rigid access port structures which may be positively gripped to facilitate rapid manipulation of the bag.

A still further object of the present invention is to provide a novel and improved plasmapheresis assembly constructed of simple, inexpensive parts which may be rapidly and safely assembled and employed to efficiently accomplish plasmapheresis.

These and other objects of the present invention will become readily apparent upon a consideration of the following specification and claims taken in conjunction with the accompanying drawings in which:

Figure 3:
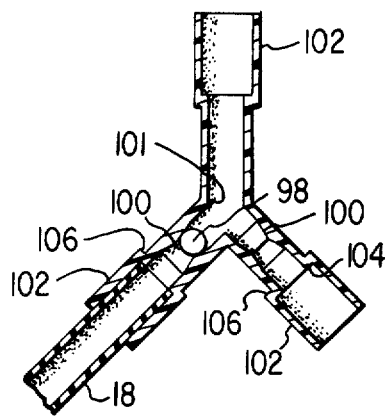
FIG. 3 is a sectional view of a Y valve for use in the assembly of FIG. 1.

Referring now to the drawings, the plasmapheresis assembly of the present invention indicated generally at 10 includes two blood collection bags 12 and 14 having inlet tubes 16 and 18 connected respectively to Y connectors 20 and 22. The Y connector 20 has branches 24a, 24b, and a branch 24c connected to the tube 16 while the Y connector 22 has branches 26a, 26b, and a branch 26c connected to the tube 18. Branch 24a of the Y connector 20 is joined by means of a tube 28 to a phlebotomy or venipuncture needle 30, while a tube 32 connects the branches 24b and 26a of the Y connectors 20 and 22. The branch 26b of the Y connector 22 receives one end of a tube 34 which terminates in a female connection or luer connector unit 36. This female connector unit is capped by a flexible cap 38 when not in use.

To accomplish a plasmapheresis procedure, the cap 38 is removed and the connector unit 36 mates with a male connector unit 40 for an administration set indicated generally at 42. This administration set includes a blood filter chamber 44 having a first inlet tube 46 connected to a container 48 for saline solution. Two other inlet tubes 50 and 52 for the blood filter chamber have free ends which are sealed to female connector units 54 and 56. A flexible outlet tube 58 from the blood filter chamber is connected to the male connector unit 40, and fluid flow through this outlet tube is controlled by an adjustable flow clamp 60.

Prior to joining connector unit 40 with connector unit 36, saline from container 48 is allowed to flow to replace the air in blood filter chamber 44 and outlet tube 58. Flow clamp 60 is then closed.

The blood collection bags 12 and 14 employed with the plasmapheresis assembly are uniquely constructed to cooperate with other sections of the assembly while providing a simple structure which may be easily fabricated and assembled from inexpensive parts. To form the collection bags, three spaced holes 62, 64 and 66 are first cut along the center line of a sheet of plastic film 68 of any suitable type conventionally used in the formation of blood collection bags. Subsequently, three short, open, tubular fitments 70, 72 and 74 having flanges 76, 78 and 80 at one end thereof are placed over individual holes of the film 68. The flanges 76, 78 and 80 are then sealed to one surface of the film, such flanges being of larger diameter than the holes 62, 64 and 66.

Once the fitments 70, 72 and 74 are sealed in place, the film is folded along the line of fitments and peripherally heat sealed along a line 82 to provide a completely enclosed container with the flanges 76, 78 and 80 on the exterior thereof. The fitments 70, 72 and 74 project from the top of the bag and are sealed to the tubes 16 and 18 and the access port assemblies for each bag. For example, the fitment 72 is sealed to a short length of tubing 84 while the fitment 74 is sealed to a short length of tubing 84. This tubing may be formed of polyvinyl chloride (PVC) or from other flexible plastic tubing which will withstand heat sterilization. All of the tubing in the plasmapheresis assembly 10 constitutes flexible tubing formed of plastic material having a similar characteristic.

Figure 1:
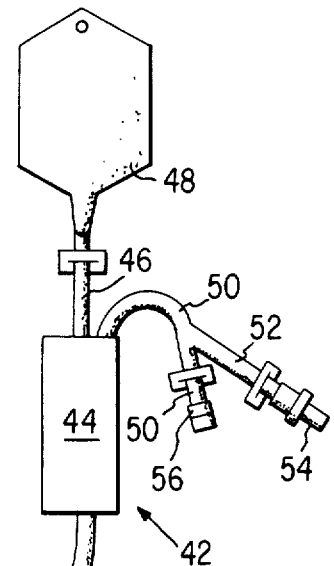
FIG. 1 is an assembly view of the plasmapheresis assembly of the present invention.
Figure 1:
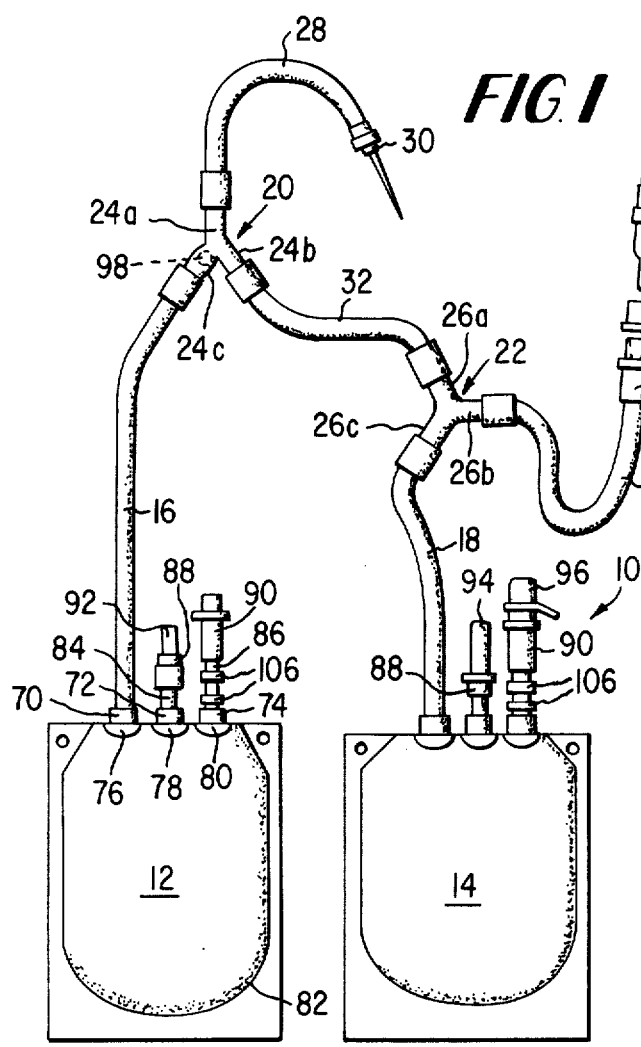
Figure 2:
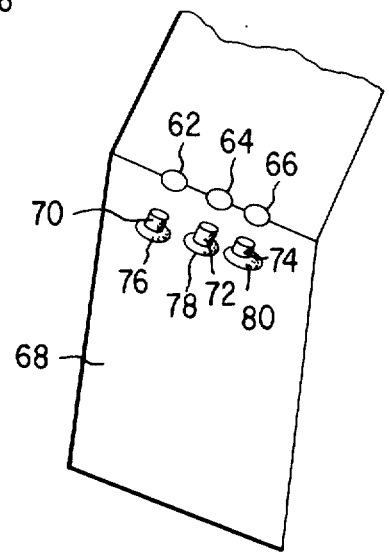
FIG. 2 is an explooded view showing the port formation for the blood containers of FIG. 1.

To complete the access ports mounted on the fitments 72 and 74, a male connector or luer connector unit 88 is sealed to the tube section 84 and a female connector or luer connector unit 90 is sealed to the tubing section 86. These connector units 88 and 90 are formed of a substantially rigid plastic material such as polycarbonate which can be solvent sealed to the PVC tubing and which also withstands heat sterilization. The connector units 36, 40, 54 and 56 are preferably formed of the same material. It should be noted that the access ports for the blood collection bags 12 and 14 which are formed by the tubes 84 and 86 and the connector units 88 and 90 extending from the fitments 72 and 74 are totally dissimilar in nature and therefore readily identifiable. The male and female connector units shown in FIG. 1 are illustrative of only one combination which may be employed for a blood collection bag, and any dissimilar connector units adapted to mate with a cooperating connector unit may be used. To enhance identification of access ports, other features may be added such as making the tube 86 longer than the tube 84 so that one access port projects above the other. In some instances, it might be possible to eliminate the tubes 84 and 86 and mount the connector units 88 and 90 directly upon the fitments 78 and 80.

The connector units 88 and 90 for the blood collection bag 12 may be identical in structure to those for the blood collection bag 14 or, in the alternative, they may be slightly modified so that the connector unit for one bag will not mate with a connector unit adapted to mate with the same connector unit of the opposite blood bag. For example, the connector unit 88 of the blood bag 14 may be formed similar to the male connector 40 while the male connector unit 88 of the blood bag 12 may contain a distinguishing structural feature, such as a square projecting tip 92. This square projecting tip will enable the connector unit 92 to mate with a mating female connector unit 56 while preventing mating of the same male connector unit with the female connector unit 54. The same would be true of the male connector unit 88 for the blood bag 14 which would mate with the female connector unit 54 but which would be precluded from mating with the female connector unit 56. When connector units 88 for bags 12 and 14 are identical, connector units 54 and 56 are of course identical.

To maintain sterility of the connector units 88 and 90 for the blood bags 12 and 14, rubber caps 94 and 96 or similar elastic caps would normally enclose the connector units when not in use as illustrated on the blood bag 14. Similar caps would be provided for all sterile connector units such as the mating female connector units 54 and 56 for the administration set 42.

The Y connector 20 provides a very important function in the operation of the plasmapheresis assembly 10, and the structure of this Y connector, will be considered with reference to FIG. 3. This Y connector is formed of flexible plastic material, such as polyvinylchloride which will withstand heat sterilization. Also, it is desirable that the Y connector be somewhat transparent so that the position of an internal ball valve 98 can be visually ascertained from the exterior of the Y connector. This ball valve is of a diameter which causes it to be held firmly is sealed relationship against the internal walls of the Y connector while permitting movement of the ball valve between branches of the connector. The firmness by which the ball valve is held should be of a degree that it will not be displaced by ordinary pressures experienced when blood flows from the donor or when saline or some other liquid is caused to flow through the set. Although the assembly in FIG. 1 shows a ball valve only in Y connector 20, connector 22 may also contain a similar ball valve. However, it is not critical in the operation of the assembly.

Since the ball valve does not move under ordinary pressures, the branches of the Y connector may be of uniform internal diameter as shown in FIG. 1. However, to assure that the ball valve does not move into branch 24b or 24c beyond a desired fixed point, these branches may be provided with a valve seat or stop 100 as shown in FIG. 3. These valve seats, which may constitute inward projections, constrictions in the connector branch, or any other structural formation to limit the inward travel of the ball valve into the branch are positioned so that the ball valve will permit communication between the two remaining branches of the Y connector while completely blocking the entrance of the third branch so that no dead space for the collection of blood is provided. Thus, the maximum distance between the entrance to any respective branch and the ball valve seat 100 for that branch is the diameter of the ball valve 98.

To assist in the movement of ball valve 98 only from branch 24b to 24c or vice versa and to assure it does not move into branch 24a, stop means may be incorporated at the juncture to branch 24a. As illustrated in FIG. 3, stop means shown at 101 takes the form of a narrowing of the internal diameter of branch 24a, or the stop means may be formed by a small internal projection.

Each branch for the Y connectors 20 and 22 terminates in a connecting hub 102 having a larger internal diameter than the internal diameter of the remaining portions of the Y connector. This results in the formation of internal circular shoulders 104 at the innermost extremity of each hub so that the end of a tube, such as the tube 18, received by one of the hubs abuts against the internal shoulder. Ideally, the inner diameter of each hub is substantially identical to the outer diameter of the tubing received thereby, while the inner diameter of the remaining portions of the Y connector containing the ball valve 98 are substantially identical to the inner diameter of the tubing. Thus, when the tubing is sealed within the hubs of the Y connector, a relatively smooth passage is provided for fluid through the connector into the tubing.

Hub 102 also has an exterior shoulder 106 which is spaced a short distance from the juncture where the three branches meet. This shoulderr 106 acts as a guide for proper positioning of the jaws of a hemostat between the shoulder and the juncture so that clamping pressure forces the ball valve from one branch to another. It also limits the positioning of a hemostat on a branch which contains no ball valve to a point very close to the juncture so that very little dead space between the juncture and the clamped area is possible for blood to clot in.

In using the plasmapheresis assembly 10, each bag 12 and 14 initially contains a measured volume (e.g., 50 ml. for a 500 ml. bag) of citrate solution which is maintained within the bags by the ball valve 98 in branch 24c of Y connector 20. The same citrate solution initially fills all connectors and connecting tubes. The single ball valve 98 prevents the flow of citrate solution from one bag to the other so as to maintain equal volumes in each bag.

Saline solution from the administration set 42, this set having been previously connected to the plasmapheresis set 10, is allowed to flow through tubes 34, 32 and 28 to clear the line of any air or, alternatively, if air resides only in tube 34, the air may be forced by the flow of saline solution through tube 18 and into bag 14. Ball valve 98 is positioned in branch 24c.

A venipuncture is made and blood is passed into the blood collection bag 14 through the tube 18. After a unit of blood has accumulated in the blood collection bag 14, the tubing 18 is sealed by RF energy or by other suitable sealing methods. The tube 18 is then severed at the seal so as to provide seals at the two severed ends and the blood collection bag 14 is centrifuged to separate the plasma from the red blood cells. The plasma is then expressed through the connector 90 into a plasma collection container having an input male connector which mates with the connector unit on the blood collection bag. The connections are easily made and in a sterile manner since there is no need to employ needles or spikes, and the flexible blood collection bag may be firmly gripped by means of the rigid connector unit 90. The tube 86 between two deformable metal clamps 106 is then severed and the sealed end together with its adjacent connector unit 90 serves as a seal for the connector unit on the plasma collection container. A hemostat may be clamped on branch 26c of Y connector 22 or, if the connector unit 22 is similar to the Y connector 20, the ball valve 98 therein would be moved to close branch 26c.

While the blood collection bag 14 is being centrifuged, it is desirable to permit saline solution to flow slowly into the donor in order to keep the blood from clotting in the needle 30.

Connector unit 88 is now mated with the connector unit 54 so that some saline solution is allowed to flow into the bag 14 to mix with the red cells. The red cell mixture is then allowed to flow through the blood filter chamber 44 and the Y connectors into the needle 30 and back into the donor. Usually a second saline solution is then introduced into the bag 14 to rinse the bag and this again is directed into the donor to be sure that essentially all of the red cells are returned. During this process, the control of flow through the tubes 46, 50 and 52 can be controlled by the manipulation of manual clamps of conventional types.

Following the return of the red blood cells to the donor, ball valve 98 in the Y connector 20 is moved from the branch 24c to the branch 24b. Now a second unit of blood is directed from the donor through the tube 16 into the blood collection bag 12. Once the second unit of blood has been collected, the ball valve is moved from the branch 24b back to the branch 24c, and tube 16 is heat sealed and severed. Saline solution is again fed to the donor while the blood collecting bag 14 is centrifuged. The plasma from the blood collection bag is removed through the connector unit 90 thereof, and then the connector unit 88 is secured to the connector unit 56. The red cells are then returned to the donor in the manner previously described. It is understood that in the procedure described above, before any cover is removed from any passageway leading to any container, that a closing means is applied to the particular passageway involved to prevent the entrance of environmental air into the system.

It is important to note that it is impossible to mistakenly connect the connector units 90 of the blood bags 12 and 14 with the connector sections 54 and 56, and therefore the introduction of contamination into the tubes 50 and 52 through error is prevented. With needle connections, it is possible to mistakenly insert a needle connected to either the tube 50 or 52 into a previously used port of the blood collection bags through which the plasma has previously been expressed. Since the sterility of this port has been destroyed through use, contamination of the blood administration set results.

Normally, the connector units 88 of the blood collection bags 12 and 14 are identical, but to positively prevent accidental insertion of the connector unit for the blood bag 14 into the connector unit 56 previously used to return the red blood cells from the blood bag 12, the connector unit 56 may be formed so as not to receive the connector unit 88 of the blood bag 14. Thus the connector unit 88 of the blood bag 12 can mate only with the connector unit 56 while that of the blood bag 14 can only mate with the connector unit 54.

The novel plasmapheresis assembly 10 of the present invention guarantees that a blood collection procedure may be performed with a minimum of possibility for bacterial contamination of the donor. The Y connector valving unit included in the assembly ensures that no dead spaces are provided for blood clotting. This valving unit also positively closes the blood bags 12 and 14 during heat sterilization to retain therein the measured volumes of citrate solution, but the flattening or distortion of the assembly tubing which often results from clamping such tubing during heat sterilization is eliminated. The rigid connector units forming the access ports for the blood collection bags facilitate positive retention and handling of the bags, while the elimination of all needle connections removes the possibility of bag puncture. The unique connector unit design prevents any mixup in a plasmapheresis procedure so that only plasma can be delivered to a plasma receiving container and only red cells can be returned to the donor. The overall assembly is designed to permit the rapid and efficient accomplishment of a blood collection procedure.

We claim:

1. A medical assembly for biological, pharmaceutical or similar fluids comprising at least one fluid container means, at least one connector means having at least first, second and third angularly disposed fluid conducting branches, said fluid conducting branches being joined at one end at a common juncture to provide connecting fluid flow paths through said branches, said connector means including internal valve means operable at said common juncture to selectively close one of said branches to all fluid flow and to open a fluid flow path between the remaining two branches, said valve means operating to completely close the end of said closed branch at the common juncture to prevent fluid from collecting in the entrance to said closed branch at said juncture and being operable to close a selected branch by movement of the valve means from the end of one of said branches through the common juncture and into the end of the selected branch to be closed, and a fluid conduit connecting said container means to one of the branches of said connector means.

2. The medical assembly of claim 1 wherein said connecttor means is formed to provide fluid conduits through said branches thereof, said valve means being formed by a ball valve movable within said connector means between the ends of the branches
at said common juncture, said ball valve being of sufficient diameter to seal said fluid conduits.

3. The medical assembly of claim 2 wherein said connector means includes a unitary body defining said fluid conducting branches, said unitary body being formed of flexible plastic material to facilitate movement of said ball valve by externally compressing said body.

4. The medical assembly of claim 3 wherein said body is formed of plastic material of sufficient transparency to permit visual determination of the position of said ball valve from the exterior of said body.

5. The medical assembly of claim 3 wherein said connector means is formed to provide tubular fluid conduits through the branches thereof, and flexible fluid conducting tubes are connected to each branch of said body, each said branch terminating in a connecting hub for receiving the end of one of said flexible tubes, each said connecting hub having a tubular inner surface of a diameter greater than the diameter of the tubular fluid conduit through the remainder of the branch.

6. The medical assembly of claim 5 wherein the diameter of the inner surface of each said hub is substantially equal to the outer diameter of the tube received thereby and the diameter of the fluid conduit through the remainder of each branch is substantially equal to the inner diameter of said tube.

7. The medical assembly of claim 1 which includes first and second fluid container means and first and second connector means, both said first and second connector means having first, second and third fluid conducting branches joined at one end at a common juncture, a first flexible tube joining said first container means to one branch of said first connector means, a second flexible tube joining said second container means to one branch of said second connector means, and a third flexible tube joining second branches of said first and second connector means.

8. The medical assembly of claim 7 which includes an administration set having an outlet tube, a fourth flexible tube being connected to a third branch of said second connector means, and joining means to connect said outlet tube with said fourth flexible tube.

9. The medical assembly of claim 8 wherein said joining means includes a first connector section on the end of said fourth flexible tube and a second connector section on the end of said outlet tube, said first and second connector sections being formed of substantially rigid material and being shaped to mate.

10. The medical assembly of claim 8 wherein each said fluid container means includes a container body of flexible, thin material defining an interior fluid fluid chamber, first and second access port means projecting outwardly from said container body, each said access port means including a connector section means formed of substantially rigid material and shaped to cooperate with a mating connector section means to form a fluid connection, the connector section means of said first access port means differing in structure from the connector section means of said second access port means.

11. The medical assembly of claim 10 wherein said administration set includes inlet means, said inlet means including mating connector section means formed to mate with the connector section means of only one access port means for each said fluid container means.

12. The medical assembly of claim 10 wherein said first access port means projects from said container body for a distance greater than said second access port means projects.

13. The medical assembly of claim 7 wherein only said first connector means includes said internal valve means.

14. The medical assembly of claim 13 which includes an administration set having an outlet tube, a fourth flexible tube being connected to a third branch of said second connector means, and joining means to connect said outlet tube with said fourth flexible tube.

15. The medical assembly of claim 7 wherein both said first and second connector means include internal valve means formed by a ball valve movable within the respective first and second connector means between the ends of the branches thereof at said common juncture, each said ball valve being of sufficient diameter to seal the fluid conduits of the respective connector means.

16. A medical assembly for biological, pharmaceutical or similar fluids comprising at least one fluid container means, at least one connector means having at least first, second and third angularly disposed fluid conducting branches joined at one end at a common juncture to provide connecting fluid conduits through said branches, said connector means including internal valve means operable at said common juncture to selectively close one of said branches to fluid flow and to open a fluid flow path between the remaining two branches, said valve means operating to completely close the end of said closed branch at the common juncture to prevent fluid from collecting in the entrance to said closed branch at said juncture and including a ball valve of sufficient diameter to seal said fluid conduits movable within said connector means between the entrance ends of said branches at the common juncture and stop means provided in at least two of said branches to limit the movement of said ball valve into the fluid conduits through said branches, said stop means in each branch being positioned inwardly from the entrance end of said branch at the common juncture for a distance substantially no greater than the diameter of said ball valve, and a fluid conduit connecting said container means to one of the branches of said connector means.

17. A medical assembly for biological, pharmaceutical or similar fluids comprising at least one container means including a container body of flexible, thin material defining an interior fluid chamber, first and second access port means projecting outwardly from said container body, each said access port means including a connector section means formed of substantially rigid material and shaped to cooperate with a mating connector section means to form a fluid connection, the connector section means of one of said access port means differing in structure from the connector section means of the remaining access port means to require unlike mating connector section means for the connector section means of said first and second access port means, at least one connector means having at least first, second and third angularly diposed fluid conducting branches, said fluid conducting branches being joined at one end at a common juncture to provide connecting fluid flow paths through said branches, said connector means including internal valve means operable at said common juncture to selectively close one of said branches to fluid flow and to open a fluid flow path between the remaining two branches, and a fluid conduit connecting said container means to one of the branches of said connector means.

18. A connector valve for joining tubing in a medical assembly comprising a connector body having a plurality of elongated angularly disposed, fluid conducting branches, each branch being joined at one end to a common juncture to provide connecting fluid conduits through said branches, and internal valve means operable at said common juncture to selectively close one of said branches to fluid flow, said valve means operating to completely close the end of said closed branch at the common juncture to prevent fluid from collecting in the entrance to the closed branch at the juncture while permitting fluid to flow in the remaining branches, said valve means including a ball valve movable within said connector body between the ends of the branches thereof at said common juncture, said ball valve being of sufficient diameter to seal said fluid conduits and stop means to limit the movement of said ball valve into the fluid conduits through said branches, the stop means being positioned within a branch inwardly from the end of said branch at the common juncture for a distance substantially no greater than the diameter of said ball valve, said connector body being formed of flexible material to facilitate movement of said ball valve by external compression of said flexible connector body.

19. The connector valve of claim 18 wherein tubular fluid conduits are formed through each of said fluid conducting branches, the outer ends of each branch terminating in an enlarged connecting hub for receiving the end of a tube, each said connecting hub having a tubular inner surface of a diameter greater than the diameter of the tubular fluid conduit through the remainder of the branch but substantially equal to the outer diameter of the tube received thereby, the diameter of the tubular fluid conduit through the remainder of the branch being substantially equal to the inner diameter of said tube.

20. The connector valve of claim 18 wherein said connector body is formed of plastic material of sufficient transparency to permit visual determination of the position of said ball valve from the exterior of said connector body.

21. A medical assembly for biological, pharmaceutical or similar fluids comprising first and second connector means each having first, second and third angularly disposed fluid conducting branches joined at one end to a common juncture to provide connecting fluid flow paths through said branches, said first connector means including internal valve means operable at said common juncture to selectively close one of said branches to fluid flow and to open a fluid flow path between the remaining two branches, first and second fluid container means each including a container body of flexible, thin material defining an interior fluid chamber, first and second access port means projecting outwardly from said container body, each such access port means including a connector section means formed of substantially rigid material and shaped to cooperate with a mating connector section means to form a fluid connection, the connector section means of said first access port means differing in structure from the connector section means of said second access port means to require unlike mating connector section means for the connector section means of said first and second access port means, a first fluid conduit joining said first container means to one branch of said first connector means, a second fluid conduit joining said second container means to one branch of said second connector means, a third fluid conduit joining second branches of said first and second connector means, and an administration set including inlet means, said inlet means including mating connector section means formed to mate with the connector section means of only one access port means for each said fluid container means and outlet means connected to a third branch of said second connector means.

22. The medical assembly of claim 21 wherein said first access port means projects from said container body for a distance greater than said second access port means projects.

* * * * *